United States Patent
Yao et al.

(10) Patent No.: US 9,188,575 B2
(45) Date of Patent: Nov. 17, 2015

(54) HOLOGRAPHIC DETECTION DEVICE AND METHOD FOR CONTENT OF GAS IN GIS SWITCH

(75) Inventors: Qiang Yao, Chongqing (CN); Xingzhe Hou, Chongqing (CN); Yulong Miao, Chongqing (CN); Ni Qiu, Chongqing (CN); Jiju Zhang, Chongqing (CN); Xiaorui Hu, Chongqing (CN)

(73) Assignee: Chongqing Electric Power Research Institute, Chongqing (CN)

( * ) Notice: Subject to any disclaimer, the term of this patent is extended or adjusted under 35 U.S.C. 154(b) by 0 days.

(21) Appl. No.: 13/699,583

(22) PCT Filed: Nov. 9, 2011

(86) PCT No.: PCT/CN2011/081980
§ 371 (c)(1),
(2), (4) Date: Jul. 12, 2013

(87) PCT Pub. No.: WO2013/053163
PCT Pub. Date: Apr. 18, 2013

(65) Prior Publication Data
US 2013/0277559 A1    Oct. 24, 2013

(30) Foreign Application Priority Data
Oct. 9, 2011    (CN) .......................... 2011 1 0303763

(51) Int. Cl.
*G01N 21/00* (2006.01)
*G01N 33/00* (2006.01)
(Continued)

(52) U.S. Cl.
CPC .......... *G01N 33/0009* (2013.01); *G01N 21/031* (2013.01); *G01N 21/359* (2013.01)

(58) Field of Classification Search
CPC .. G01N 21/359; G01N 21/39; G01N 21/3504
USPC .............. 250/338.1–338.5, 340, 341.1–341.8
See application file for complete search history.

(56) References Cited

U.S. PATENT DOCUMENTS 4,535,241 A * 8/1985 Eberhardt ................ 250/339.13
5,705,816 A   1/1998 Ronge et al.
(Continued)

FOREIGN PATENT DOCUMENTS

| CN | 2620372 Y | 6/2004 |
| CN | 1851447 A | 10/2006 |
| JP | 2004170245 A * | 6/2004 |

OTHER PUBLICATIONS

International Search Report for PCT Application PCT/CN2011/081980 mailed Jun. 7, 2012.
(Continued)

*Primary Examiner* — Kiho Kim
(74) *Attorney, Agent, or Firm* — Greenberg Traurig, LLP; David J. Dykeman

(57) ABSTRACT

A holographic detection device for a content of a gas in a GIS switch includes a laser and a data process system. The laser includes a laser emitter and a laser receiver which are fixed at a sampling port of the GIS switch and connected with the data process system. A holographic detection method for a content of a gas in a GIS switch includes emitting a laser beam towards the inside of the GIS switch; receiving the laser beam from the inside of the GIS switch, and calculating a content of hydrogen fluoride gas inside the GIS switch according to an intensity of the emitted laser beam and an intensity of the received laser beam. Since the laser beam goes through the inside of the GIS switch, there is a small error in the detection result, which thus can reflect a real state inside the GIS switch.

11 Claims, 7 Drawing Sheets

(51) Int. Cl.
*G01N 21/03* (2006.01)
*G01N 21/359* (2014.01)

(56) References Cited

U.S. PATENT DOCUMENTS

| | | | | |
|---|---|---|---|---|
| 6,101,200 | A | * | 8/2000 | Burbidge et al. ........ 372/29.021 |
| 6,121,627 | A | * | 9/2000 | Tulip .......................... 250/559.4 |
| 6,202,470 | B1 | * | 3/2001 | Chou ............................. 73/24.02 |
| 6,313,464 | B1 | * | 11/2001 | Schrader ....................... 250/349 |
| 7,504,631 | B2 | * | 3/2009 | May ........................... 250/339.1 |
| 7,916,395 | B2 | * | 3/2011 | Cole .............................. 359/584 |
| 8,013,303 | B2 | | 9/2011 | Ershov et al. |
| 8,614,096 | B2 | * | 12/2013 | Alvarez et al. ................ 436/101 |
| 2004/0039084 | A1 | * | 2/2004 | Beisele ......................... 523/201 |
| 2006/0124852 | A1 | * | 6/2006 | Von Drasek ............. 250/339.13 |

OTHER PUBLICATIONS

Dahai, et al., "On-line application of laser gas analyzer based on DLAS technology", Fuel & Chemical Processes, vol. 40, No. 5, pp. 14-17, (2009).

Wei, et al., "Application of in situ laser gas analyzer in process control of blast furnace", Metallurgical Industry Automation, No. 2, pp. 33-36, (2006).

Wang, et al., "Application of Laser Gas Analyzer in Recovery of converter Gas", Metallurgical Power; vol. 1, No. 131, pp. 21-22, (2009).

\* cited by examiner

US 9,188,575 B2

HOLOGRAPHIC DETECTION DEVICE AND METHOD FOR CONTENT OF GAS IN GIS SWITCH

RELATED APPLICATIONS

This application is a national phase filing under 35 U.S.C. 371 of International Application No. PCT/CN2011/081980, filed on Nov. 9, 2011, which claims the benefit of and priority to Chinese Patent Application No. 201110303763.X, entitled "HOLOGRAPHIC DETECTION DEVICE AND METHOD FOR CONTENT OF GAS IN GIS SWITCH", filed with the Chinese Patent Office on Oct. 9, 2011, which applications are hereby incorporated by reference in its their entirety.

FIELD

The present disclosure relates to the field of the detection of a component of a characteristic gas in electrical equipment, and in particular to a holographic detection device and method for content of gas in a GIS switch.

BACKGROUND

Since the 1970's, electric equipment with an insulation medium of sulfur hexafluoride ($SF_6$) gas has been widely used. However, due to the limitation of design, material, process and maintenance, etc., local insulation defect may exist inside the equipment. Under heat and electricity, $SF_6$ gas and solid insulation material are decomposed continuously, such that the insulation performance is decreased and an accident even occurs. Therefore, one of the key researches of the electric power professionals is to detect a potential fault and danger inside the electric equipment at the first opportunity and decrease the accident rate.

Based on the research, when a fault appears in electric equipment with $SF_6$, characteristic components such as $SO_2$, $SOF_2$, $H_2S$, CO, HF and $CF_4$ will be generated in the fault section. Since the hydrogen fluoride (HF) gas is generated firstly, the fault in the electric equipment can be determined by detecting the content of the HF gas.

The Gas Insulated Switchgear, i.e., GIS switch, is a combined electric equipment with an insulation medium of sulfur hexafluoride ($SF_6$) gas. In the prior art, the method for detecting the HF gas inside the GIS switch is to obtain a gas sample at a sampling port of the GIS switch by a sampling bag and detect the content of HF in the gas sample by a corresponding detection instrument. However, since the GIS switch has a huge volume, a small internal temperature difference and a poor gas fluidity, a little gas sample obtained from the sampling port far away from the body of the electric equipment is not a representative sample, the detection result of the gas sample is not exact and hard to reflect a real state inside the GIS switch. Therefore, it is hard to detect a potential fault inside the GIS switch in time. Furthermore, since the sampling period is long (generally once in spring and once in autumn), a potential fault inside the GIS switch cannot be detected in time either.

SUMMARY

Therefore, an object of an embodiment of the present disclosure is to provide a holographic detection device and method for content of gas in a GIS switch, to solve problems of the existing sampling bag method that the obtained gas sample can not be a representative sample because the sampling port is far away from the body of the device and that the detected result is not exact.

In order to achieve the above purpose, an embodiment of the present disclosure provides the following schemes.

A holographic detection device for a content of a gas in a GIS switch includes a laser device and a data process system, the laser includes a laser emitter and a laser receiver which are fixed at a sampling port of the GIS switch by a flange and connected with the data process system by an optical cable; where the laser emitter is adapted to emit a laser beam towards the inside of the GIS switch;

the laser receiver is adapted to receive the laser beam emitted from the laser emitter and coming from the inside of the GIS switch;

the data process system is adapted to calculate the content of hydrogen fluoride gas inside the GIS switch according to an intensity of the laser beam emitted from the laser emitter and an intensity of the laser beam received by the laser receiver.

Preferably, the holographic detection device for a content of a gas in a GIS switch further includes a laser assistant unit which includes a temperature control module, a current control module and a signal generator.

Preferably, the laser emitter is a tunable semiconductor laser with a center wavelength of 2476 nm.

Preferably, the data process system is a central process system matching with the tunable semiconductor laser.

Preferably, the laser emitter and the laser receiver are fixed at a sampling port or at separate sampling ports.

A holographic detection method for a content of a gas in a GIS switch includes:

emitting a laser beam towards the inside of the GIS switch;
receiving the laser beam from the inside of the GIS switch; and
calculating a content of hydrogen fluoride gas inside the GIS switch according to an intensity of the emitted laser beam and an intensity of the received laser beam.

Preferably, the emitted laser beam is reflected at an inner wall of the GIS switch and emerged, after being emitted into the inside of the GIS switch.

Preferably, a wavelength of the laser beam is 2476±1 nm.

Preferably, a specific implement of emitting the laser beam into the GIS switch includes:

tuning the wavelength of the laser beam emitted from the tunable semiconductor laser to 2476±1 nm by a laser assistant unit, and emitting the laser beam with a wavelength of 2476±1 nm into the GIS switch by the tunable semiconductor laser.

Preferably, a specific implement of calculating the content of hydrogen fluoride gas inside the GIS switch according to the intensity of the emitted laser beam and the intensity of the received laser beam includes:

obtaining the intensity $I_0$ of the emitted laser beam and the intensity I of the received laser beam;
calculating a total length L of an optical path of the laser beam in the GIS switch;
calculating the content of hydrogen fluoride gas in the GIS switch according to $C = \ln(I_0/I)/\alpha(\lambda) L$, where $\lambda$ is a wavelength of the laser beam, $\alpha(\lambda)$ is an absorption coefficient of the hydrogen fluoride gas per unit length and per unit concentration.

As can be seen from the above technical scheme, in an embodiment of the present disclosure, a laser emitter emits a laser beam into the inside of the GIS switch, and the above emitted laser beam is finally received by a laser receiver. A data process system may calculate the content of hydrogen fluoride gas into the GIS switch by the intensity of the emitted and received laser beam, so as to implement a sampling. Meanwhile, since the optical path of the laser beam passes through the inside of the GIS switch, there is a small error of the calculation result, which can reflect a real state inside the GIS switch. Further, in the present disclosure, the device is simply operated, not affected by pressure inside the GIS switch and can always be in an operation state, so as to detect a potential fault inside the GIS switch in time and provide exact original data.

DETAILED DESCRIPTION

A clear and full description of technical solutions of embodiments of the present disclosure is made below in conjunction with drawings of embodiments of the present disclosure. Apparently, the described embodiments are merely parts of embodiments and not all of embodiments of the present disclosure. Based on embodiments of the present disclosure, all other embodiments obtained by those skilled in the art without creative labor are all belong to the protection scope of the present disclosure.

An embodiment of the present disclosure discloses a holographic detection device and method for content of gas in a GIS switch, to solve problems of the existing sampling bag method that there is a large detection error and a potential fault in the GIS switch cannot be detected in time because the sampling port is far away from the body of the device.

Figure 1:
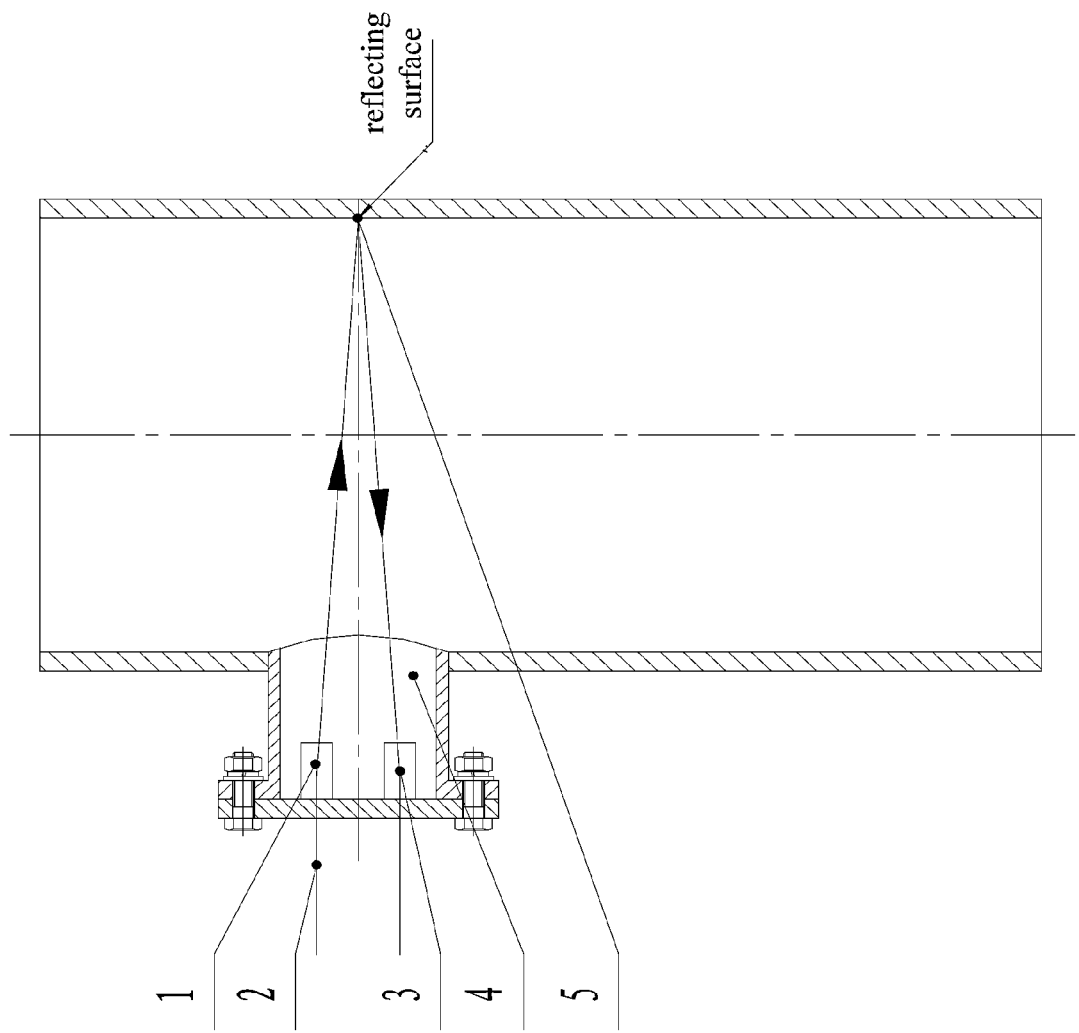
FIG. 1 is a schematic structure diagram of a holographic detection device for content of gas in a GIS switch according to an embodiment of the present disclosure.

FIG. 1 illustrates a structure of the above holographic detection device for content of gas in a GIS switch, which includes a laser and a data process system. The laser includes a laser emitter 1 and a laser receiver 3 which are fixed at a sampling port 4 of the GIS switch by a flange and connected with the data process system by an optical cable 2.

Particularly, the laser emitter 1 may be used for emitting a laser beam towards the inside of the GIS switch; the laser receiver 3 may be used for receiving the laser beam emitted from the laser emitter 1 and coming from the inside of the above GIS switch; the data process system is used for calculating a content of hydrogen fluoride gas inside the GIS switch according to an intensity of the laser beam emitted from the laser emitter 1 and an intensity of the laser beam received by the laser receiver 3.

Figure 2:
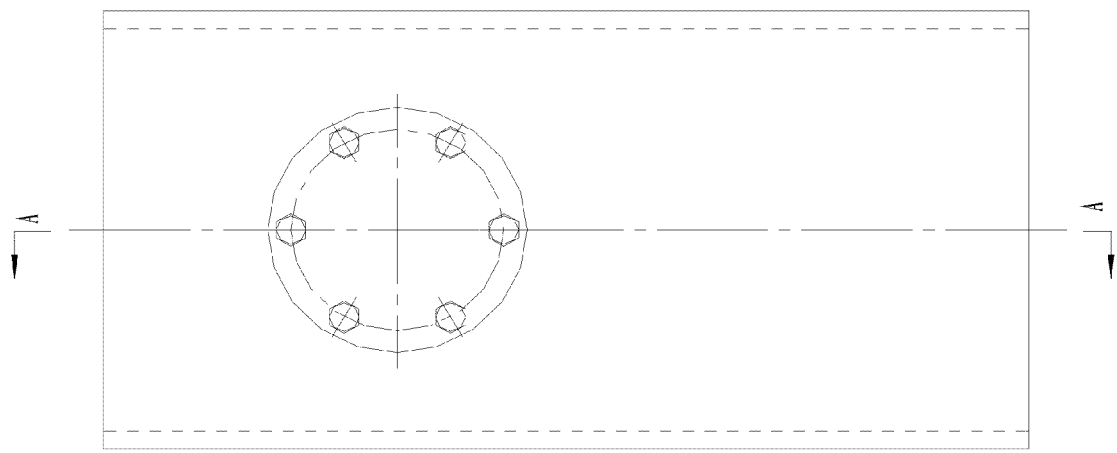
FIG. 2 is a schematic installation diagram of a holographic detection device for content of gas in a GIS switch according to an embodiment of the present disclosure.

FIG. 2 illustrates an installation manner of the above device. A flange on which the laser emitter 1 and the laser receiver 3 are fixed is fastened with a flange at the sampling port 4 by a bolt.

It can be seen that in an embodiment of the present disclosure, the laser emitter emits the laser beam into the inside of the GIS switch, and the above emitted laser beam is finally received by the laser receiver. The data process system can calculate the content of hydrogen fluoride gas inside the GIS switch according to the intensity of the emitted and received laser beam, so as to implement the sampling. Meanwhile, since the optical path of the laser beam passes through the inside of the GIS switch, there is a small error of the calculation result, which can reflect a real state inside the GIS switch. Further, the above device is simply operated, not affected by pressure inside the GIS switch and can always be in an operation state, so as to detect a potential fault inside the GIS switch in time and provide exact original data.

In other embodiments of the present disclosure, the holographic detection device for content of gas in a GIS switch further includes a laser assistant unit. The laser assistant unit includes a temperature control module, a current control module and a signal generator, which separately provide compensation, control and excitation to the laser. Since the HF gas has a good absorption performance under a wavelength of 2476±1 nm, which is not interfered by background gas of $SF_6$. The above laser emitter 1 can specifically be a tunable semiconductor laser with a centre wavelength of 2476 nm.

Based on the above laser assistant unit and the tunable semiconductor laser, a specific method for tuning the wavelength of the laser beam includes: tuning the output wavelength of the tunable semiconductor laser to about 2476 nm by the temperature control module and the current control module; outputting a sawtooth wave signal with a frequency of 50 Hz by the signal generator and superposing the signal on the drive current of the tunable laser, so as to perform the wavelength scan within a range of 2476±1 nm by the tunable semiconductor laser and emit a laser beam with a wavelength of 2476±1 nm.

In other embodiments of the present disclosure, the data process system in the above embodiments may specifically be a central process system matching with the tunable semiconductor laser.

In other embodiments of the present disclosure, referring to FIG. 1 again, the laser emitter 1 and the laser receiver 3 in the above embodiments can be fixed at a sampling port 4 by a flange. The laser beam emitted from the laser emitter 1 is reflected by a reflection surface 5 into the GIS switch once and emerged, and then received by the laser receiver 3.

Since the relative position of the laser emitter 1 and the laser receiver 3 is fixed and irremovable after the device is installed, the laser emitter 1 should ensure that the incident angle of the laser beam is a specific angle a when emitting the laser beam, so as to ensure that the laser receiver 3 can receive the single-reflected laser beam. The calculation of the specific incident angle a is as following.

Figure 3:
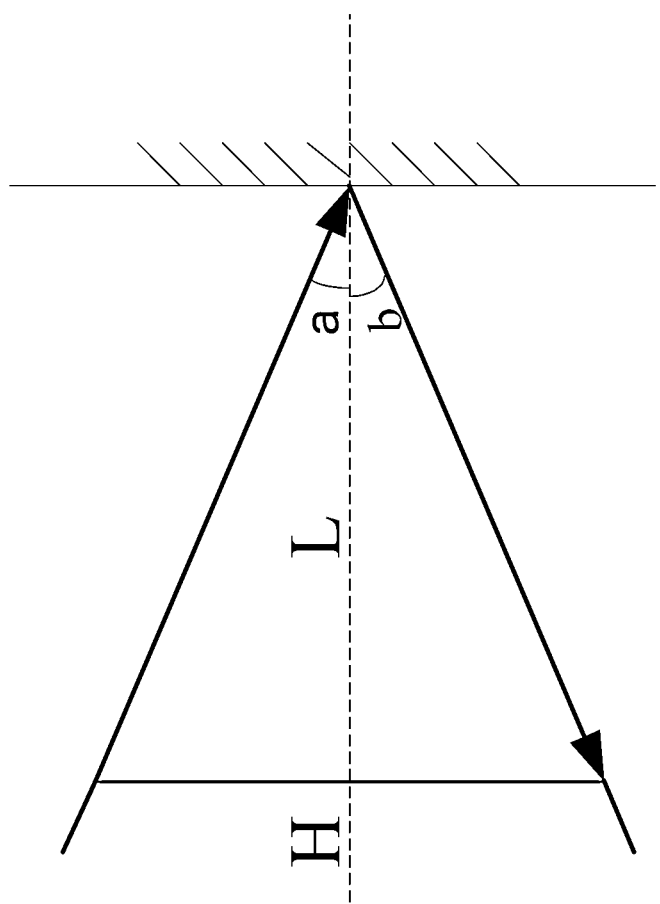
FIG. 3 is a schematic diagram of calculating a specific incident angle of a laser beam according to an embodiment of the present disclosure.

Referring to FIG. 3, assuming that H is the center distance of the laser emitter 1 and the laser receiver 3, L is the vertical distance from the middle point of H to the reflecting surface. Apparently, H and L are invariable and known quantity after the device is installed. According to law of reflection (the reflection ray, the incident ray and the normal are on a same plane; the reflection ray and the incident ray are at two sides of the normal; and the reflection angle is equal to the incident angle), the above specific incident angle a is a=acrtan(0.5 H/L).

In addition, in other embodiments of the present disclosure, the laser emitter 1 and the laser receiver 3 may be fixed at different sampling ports. In this case, the laser beam emitted from the laser emitter 1 may be reflected N (N is an odd number) times at inner walls of the GIS switch and emerged, and then received by the laser receiver 3. In this way, the above specific incident angle a is a=acrtan[H/((N+1)L)].

Figure 4:
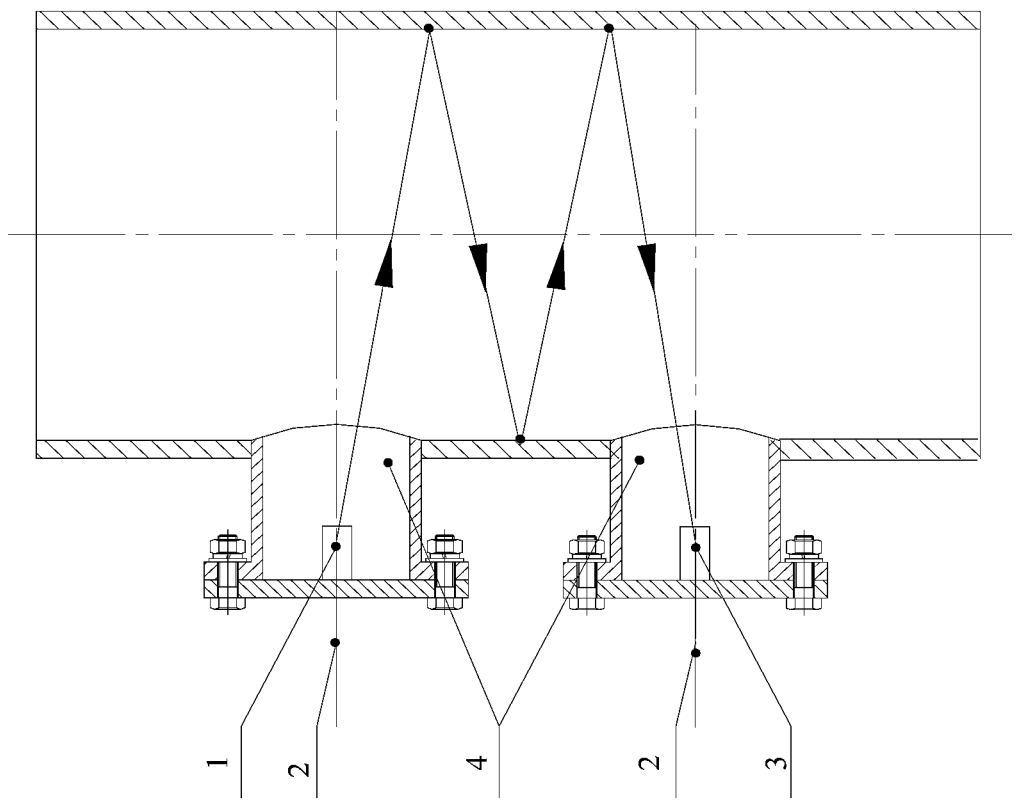
FIG. 4 is another schematic structure diagram of a holographic detection device for content of gas in a GIS switch according to an embodiment of the present disclosure.
Figure 5:
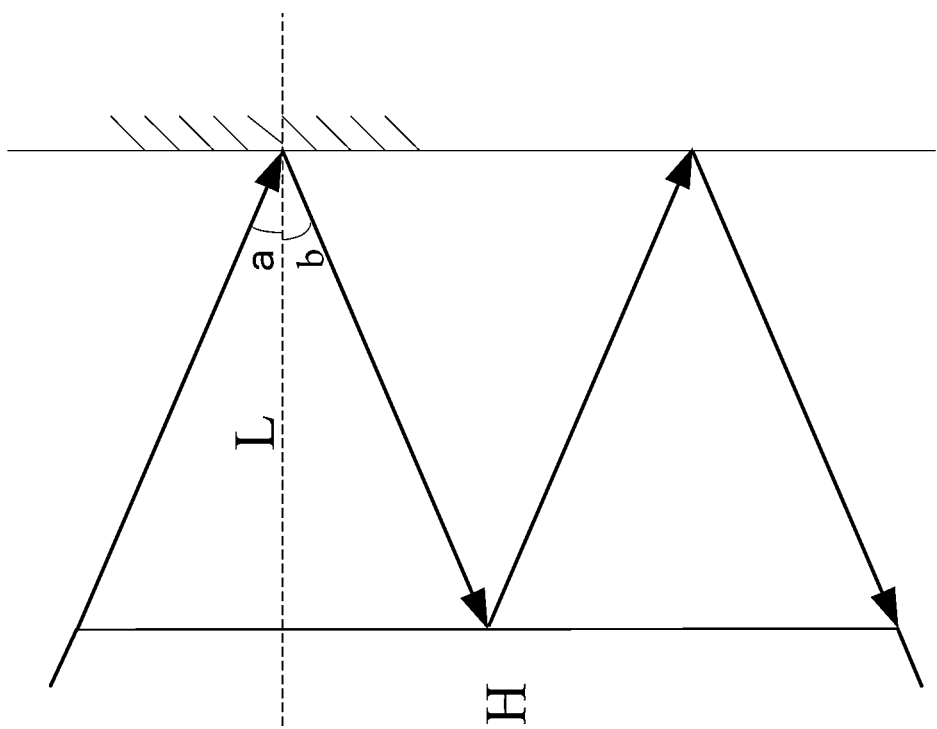
FIG. 5 is a schematic diagram of calculating a specific incident angle of a laser beam according to an embodiment of the present disclosure.

For example, N=3, i.e., there are three times of reflection, the corresponding incident angle a is a=acrtan(0.25 H/L), referring to FIG. 4 and FIG. 5.

Figure 6:
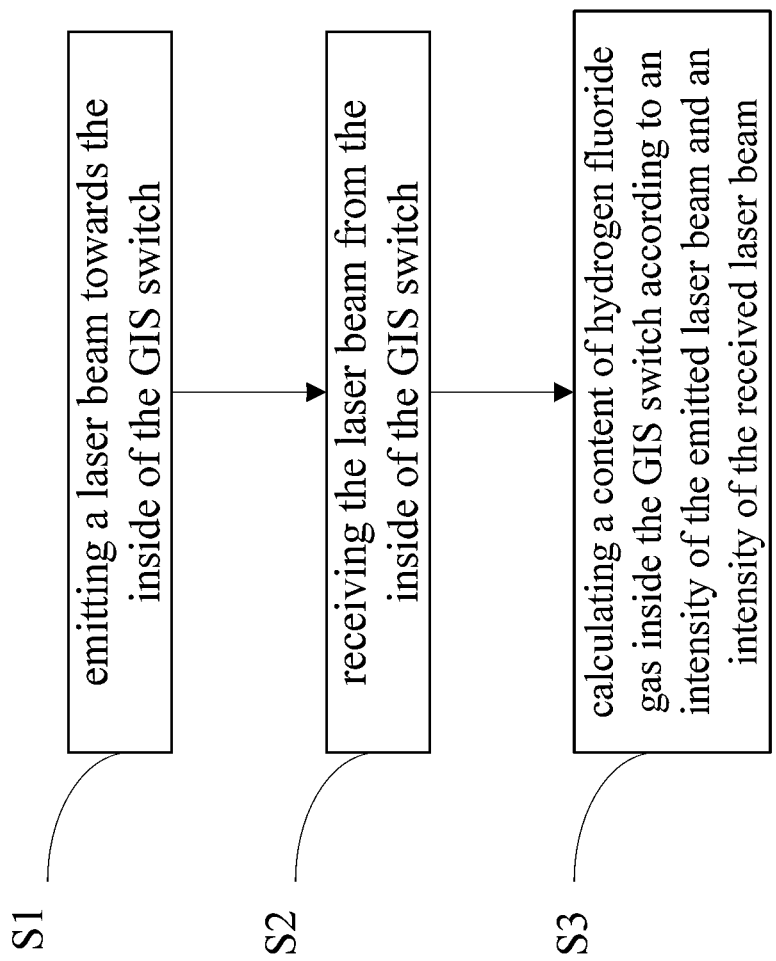
FIG. 6 is a flow chart of a holographic detection method for content of gas in a GIS switch according to an embodiment of the present disclosure.

According to the above device, an embodiment of the present disclosure provides a holographic detection method for a content of a gas in a GIS switch, referring to FIG. 6. The method at least includes the following steps:

S1: emitting a laser beam towards the inside of the GIS switch;

S2: receiving the laser beam from the inside of the GIS switch; and

S3: calculating a content of hydrogen fluoride gas inside the GIS switch according to an intensity of the emitted laser beam and an intensity of the received laser beam.

In the above method, the emitted laser beam has a wavelength of 2476±1 nm. The emitted laser beam is reflected at an inner wall of the GIS switch and emerged after being emitted into the inside of the GIS switch.

Particularly, a specific method of emitting the laser beam with a wavelength of 2476±1 nm towards the inside of the GIS switch includes: tuning the output center wavelength of the tunable semiconductor laser to 2476±1 nm by a laser assistant unit which includes a temperature control module, a current control module and a signal generator, and emitting the laser beam with a wavelength of 2476±1 nm towards the inside of the GIS switch by the tunable semiconductor laser.

In other embodiments of the present disclosure, a specific implementation of the above step S3 may include: calculating the content of hydrogen fluoride gas inside the GIS switch by a central process system matching with the above tunable semiconductor laser according to the intensity of the emitted laser beam and the intensity of the received laser beam.

Figure 7:
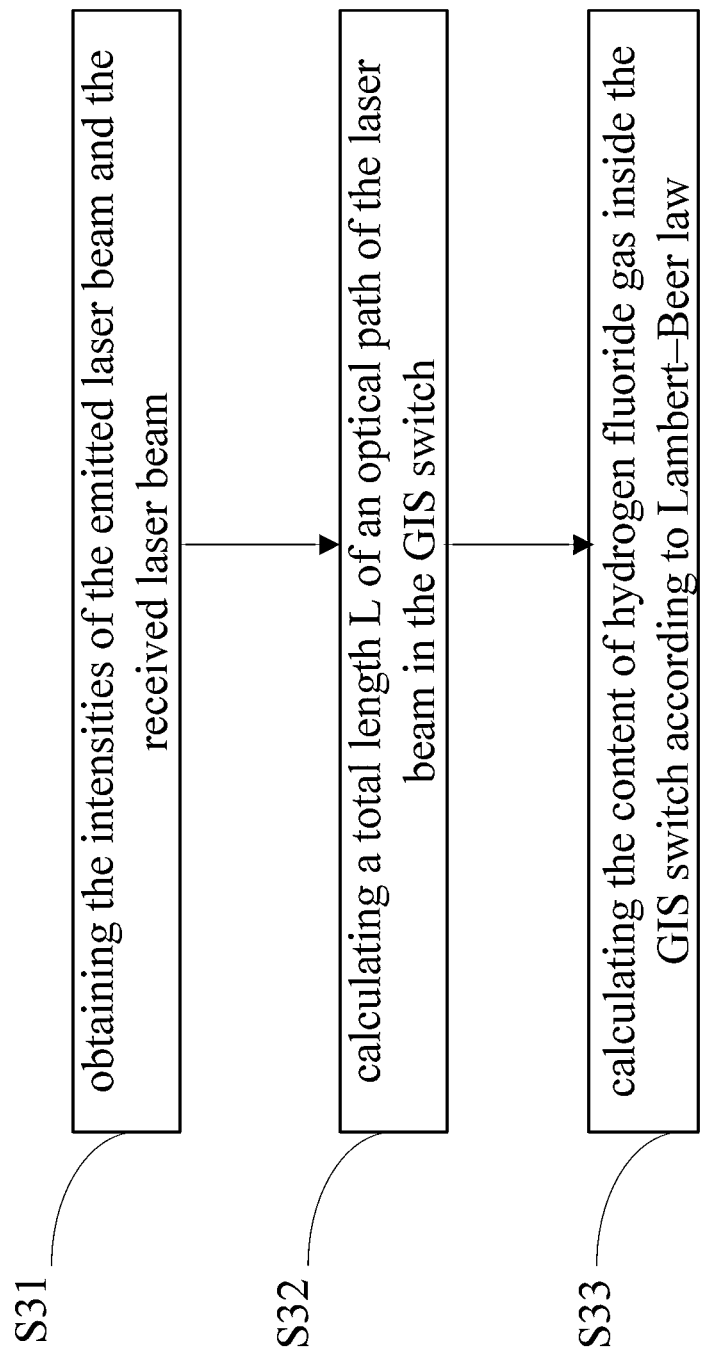
FIG. 7 is a flow chart of calculating a content of hydrogen fluoride gas according to an embodiment of the present disclosure.

In other embodiments of the present disclosure, referring to FIG. 7, the step of calculating the content of hydrogen fluoride gas inside the GIS switch by the central process system may specifically include:

S31: obtaining the intensities of the emitted laser beam and the received laser beam;

S32: calculating a total length L of an optical path of the laser beam in the GIS switch,
where L can be calculated according to the incident angle a of the laser beam, the times of reflection N of the laser beam inside the GIS switch and the distance H between the emitted point and the received point of the laser beam; and S33: calculating the content of hydrogen fluoride gas inside the GIS switch according to Lambert-Beer law.

The Lambert-Beer law is: $I=I_0 \exp[-\alpha(\lambda)CL]$, where $I_0$ is the intensity of the laser beam with a wavelength of $\lambda$, when there is no the gas to be detected, C is a concentration of an absorption gas, $\alpha(\lambda)$ is an absorption coefficient of the gas per unit length and per unit concentration. Therefore, according to the above method provided by an embodiment of the present disclosure, the concentration of the hydrogen fluoride gas $C=\ln(I_0/I)/(\alpha(\lambda)L)$, where $I_0$ is the intensity of the emitted laser; I is the intensity of the received laser beam; $\lambda$ is the wavelength of the laser beam, i.e., 2476 nm; L is the total length of the optical path of the laser beam, and $\alpha(\lambda)$ is an absorption coefficient of hydrogen fluoride gas per unit length and per unit concentration.

Those skilled in the art can implement or use the present disclosure according to the above description of the disclosed embodiments. Various amendments to those embodiments are obvious for those skilled in the art. A general principle defined herein may be implemented in other embodiments without departing from the spirit or scope of the present disclosure. Therefore, the present disclosure is not limited to those illustrated embodiments in the disclosure, and is accorded with a broadest scope consistent with the principle of the present disclosure and the novelty feature.

The invention claimed is:

1. A holographic detection device for a content of a gas in a GIS switch, comprising:
   a laser and a data process system, wherein the laser comprises a laser emitter and a laser receiver which are fixed at a sampling port of the GIS switch by a flange, and connected with the data process system by an optical cable, and
   wherein the laser emitter is adapted to emit a laser beam towards inside of the GIS switch;
   the laser receiver is adapted to receive the laser beam emitted from the laser emitter and coming from the inside of the GIS switch; and
   the data process system is adapted to calculate the content of hydrogen fluoride gas inside the GIS switch according to an intensity of the laser beam emitted from the laser emitter and an intensity of the laser beam received by the laser receiver, and
   wherein the laser emitter is a tunable semiconductor laser with a center wavelength of 2476 nm.

2. The device according to claim 1, further comprises a laser assistant unit which comprises a temperature control module, a current control module and a signal generator.

3. The device according to claim 1, wherein the data process system is a central process system matching with the tunable semiconductor laser.

4. The device according to claim 1, wherein the laser emitter and the laser receiver are fixed at separate sampling ports of the GIS switch.

5. A holographic detection method for a contact of a gas in a GIS switch, comprising:
   providing a laser emitter and a laser receiver fixed at a sampling port of the GIS switch;
   emitting, by the laser emitter, a laser beam towards the inside of the GIS switch, wherein the laser emitter is a tunable semiconductor laser with a center wavelength of 2476 nm;
   receiving, by the laser receiver, the laser beam from the inside of the GIS switch, and
   calculating a content of hydrogen fluoride gas inside the GIS switch according to an intensity of the emitted laser beam and an intensity of the received laser beam.

6. The method according to claim 5, wherein the laser beam is reflected at an inner wall of the GIS switch and emerged, after being emitted into the inside of the GIS switch.

7. The method according to claim 5, wherein a step of emitting the laser beam towards the inside of the GIS switch comprises:
   tuning the wavelength of the laser beam emitted from the tunable semiconductor laser to 2476±1 nm by a laser assistant unit, and emitting the laser beam with a wavelength of 2476±1 nm towards the inside of the GIS switch by the tunable semiconductor laser.

8. The method according to claim 7, wherein a step of calculating the content of hydrogen fluoride gas inside the GIS switch according to the intensity of the emitted laser beam and the intensity of the received laser beam comprises:

obtaining the intensity $I_0$ of the emitted laser beam and the intensity I of the received laser beam;

calculating a total length L of an optical path of the laser beam in the GIS switch; and calculating the content of hydrogen fluoride gas inside the GIS switch according to $C=\ln(I_0/I)/\alpha(\lambda)L$, wherein $\lambda$ is the wavelength of the laser beam, $\alpha(\lambda)$ is an absorption coefficient of the hydrogen fluoride gas per unit length and per unit concentration.

9. A detection device for a content of a gas in a GIS switch, comprising:

a laser and a data process system, wherein the laser comprises a laser emitter and a laser receiver which are fixed at a sampling port of the GIS switch, and in communication with the data process system, wherein the laser emitter is adapted to emit a laser beam towards an inside of the GIS switch, and wherein the laser emitter is a tunable semiconductor laser with a center wavelength of about 2476 nm;

the laser receiver is adapted to receive the laser beam emitted from the laser emitter and coming from the inside of the GIS switch; and the data process system is adapted to calculate the content of hydrogen fluoride gas inside the GIS switch according to an intensity of the laser beam emitted from the laser emitter and an intensity of the laser beam received by the laser receiver.

10. The detection device according to claim 9, wherein the laser emitter and the laser receiver are fixed at the sampling port of the GIS switch by a flange and connected with the data process system by an optical cable.

11. The detection device according to claim 9, wherein the laser emitter and the laser receiver are fixed at separate sampling ports of the GIS switch.

* * * * *